United States Patent [19]

Sakai

[11] Patent Number: 4,509,034
[45] Date of Patent: Apr. 2, 1985

[54] GAS SENSOR

[75] Inventor: Sai Sakai, Osaka, Japan

[73] Assignee: New Cosmos Electric Col, Ltd., Japan

[21] Appl. No.: 579,926

[22] Filed: Feb. 14, 1984

[30] Foreign Application Priority Data

Mar. 22, 1983 [JP] Japan ............................ 58-39724[U]
Jun. 28, 1983 [JP] Japan ............................ 58-98725[U]

[51] Int. Cl.³ ............................................ G01N 27/12
[52] U.S. Cl. ............................................ 338/34; 73/23;
73/27 R; 422/98
[58] Field of Search ............ 338/34, 35; 73/23, 27 R;
422/94, 98

[56] References Cited

U.S. PATENT DOCUMENTS 4,206,173  6/1980  Yamaguchi et al. ............ 338/34 X
4,242,302 12/1980  Kitamura et al. ................ 338/34 X
4,313,338  2/1982  Abe et al. ................................ 73/23
4,396,899  8/1983  Ohno ..................................... 338/34

FOREIGN PATENT DOCUMENTS 56-08538  1/1981  Japan ..................................... 338/34
56-51656  5/1981  Japan ..................................... 338/34

OTHER PUBLICATIONS

Pink et al., "Preparation of Fast Detecting SnO₂ Gas Sensors", Japanese Journal of Applied Physics, vol. 19, No. 3, Mar. 1980, pp. 513-517.

Primary Examiner—Roy N. Envall, Jr.
Assistant Examiner—C. N. Sears
Attorney, Agent, or Firm—Jones, Tullar & Cooper

[57] ABSTRACT

A gas sensor comprising an electric resistor of noble metal and a sintered piece of a metal oxide covering the resistor and serving as a semiconductor. The ratio of the combined resistance Ro of the resistor and the semiconductor to the resistance ro of the resistor, Ro/ro, is within the range of $0.45 < Ro/ro < 0.95$. The sintered piece may be prepared from a mixture of $SnO_2$ powder of usual particle sizes and a superfine powder of $SnO_2$ by sintering the mixture at about 600° C. to about 800° C.

7 Claims, 7 Drawing Figures

GAS SENSOR

BACKGROUND OF THE INVENTION

The present invention relates to a gas sensor.

Most gas sensors which comprise a semiconductor of oxide such as $SnO_2$, $ZnO$, $Fe_2O_3$ or $In_2O_3$ and which are commercially available or under investigation for development at present require two kinds of electrodes, i.e., a sensor electrode and a heater, whether the sensor is of the thick layer type, the film type or the sintered chip type. Such sensors necessitate a complicated manufacturing process and are costly because they generally comprise a base plate, sensing and heating film electrodes formed on the front surface and the rear surface of the base plate respectively, and four lead wires. Another gas sensor is known which comprises an electrode of platinum film formed on a quartz tube and trimmed in a spiral form, a gas sensing layer of metal oxide semiconductor covering the entire electrode and a heater disposed within the quartz tube. This sensor also has the disadvantage of requiring four lead wires and two power supplies for the sensor electrode and the heater.

On the other hand, known composite sensors include one comprising two gas sensing units having a semiconductor adhered to a coiled resistor, i.e., a heating wire, a gas sensing activity, although a high sintering temperature of at least 1000° C. is required to give a product of high strength. Consequently the sintered piece has exceedingly lower strength than usual ceramics, failing to have mechanical strength sufficient to withstand the impact or vibration to be usually exerted thereon during use. Various proposals have therefore been made to provide gas sensors of improved mechanical strength, while silica prepared from an organosilicon compound is presently used as a binder for commercial gas sensors. Silica sol or the like is also used for others which are in the stage of research and development. However, when such a binder is used for sintering, $SiO_2$ or $Al_2O_3$ remains in the product. Since the silica or alumina is hydrophilic, the gas sensitivity of the sensor obtained is dependent largely on humidity and varies with time when the sensor is exposed to a highly humid atmosphere.

SUMMARY OF THE INVENTION

Accordingly, the main object of the present invention is to provide a highly sensitive gas sensor in which a single electric resistor serves as a heater and also as an electrode (sensor electrode) for detecting the variation of resistance due to the adsorption of gas so that one of the two power supplies conventionally used can be dispensed with to render the sensor less costly.

According to the present invention, an electric resistor of noble metal formed on a heat-resistant electrically insulating base plate is covered with an oxide semiconductor. When electric current is passed through the resistor in the atmosphere, the ratio of the combined resistance Ro of the resistor and the oxide semiconductor to the resistance ro of the resistor is in the range of $0.3 < Ro/ro < 0.98$, preferably in the range of $0.45 < Ro/ro < 0.95$. The ratio Ro/ro can be made a desired value by adjusting the specific resistance of the powder for forming the oxide semiconductor, for example, with use of a very small amount of antimony pentoxide when tin oxide is sintered into a piece.

Another object of the present invention is to provide a gas sensor having the foregoing Ro/ro ratio and comprising an oxide semiconductor which is prepared by sintering tin oxide particles of usual size with use of a binder consisting predominantly of a superfine powder of tin oxide. A content of the superfine powder in a sintered piece is preferably about 10 to about 50%, and more desirably about 30% by weight of the sintered piece.

According to the invention, the oxide semiconductor, i.e. the sintered piece of tin oxide, has an improved mechanical strength, while the gas sensitivity of the sensor has a reduced humidity dependence.

The noble metal resistor may be in the form of a thin film or a coiled wire.

Other objects and advantages of the present invention will become apprent from the following description of embodiments with reference to the accompanying drawings.

DESCRIPTION OF THE PREFERRED EMBODIMENTS

First Embodiment

Figure 1:
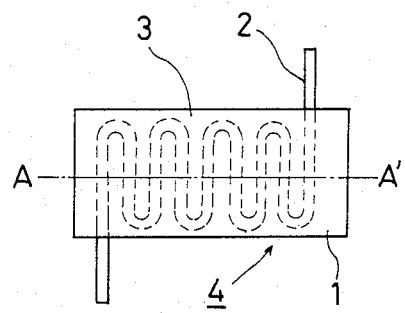
FIG. 1 is a plan view showing a gas sensor of a first embodiment of the invention.
Figure 2:
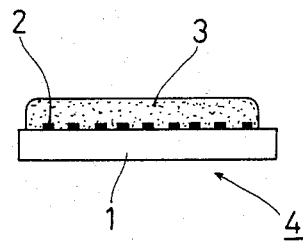
FIG. 2 is a view in cross section taken along the line A—A' in FIG. 1.

With reference to FIGS. 1 and 2, a platinum (Pt) film resistor 2 is formed in a zigzag shape on an alumina base plate 1 by vapor deposition. A sintered stannic oxide ($SnO_2$) piece 3 covering the resistor 2 is formed over the alumina base plate 1. Thus, a gas sensor 4 comprises the base plate 1, resistor 2 and sintered piece 3.

The resistor (hereinafter referred to as "electrode") 2 serves as a gas detecting electrode and also as a heater. The specific resistance of the powder used for the sintered piece 3 is so determined as to provide an optimum relationship between the resistance of the electrode 2 and that of the sintered piece 3. This diminishes the temperature change of the gas sensor 4 during its contact with gas, permitting the sensor 4 to deliver an output with high sensitivity.

Stated more specifically, the specific resistance of the $SnO_2$ powder and the sintering conditions are so selected that the ratio Ro/ro is within the range defined by the inequality $0.3 < Ro/ro < 0.98$, preferably within the range defined by the inequality $0.45 < Ro/ro < 0.95$, wherein ro is the resistance of the resistor 2, and Ro is the combined resistance of the electrode 2 and the sintered piece 3.

Figure 3:
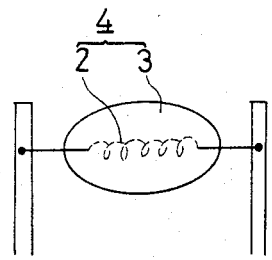
FIG. 3 is a front view showing a modification of the first embodiment.

The electrode included in the gas sensor is not limited to a thin film formed on the base plate as seen in FIGS. 1 and 2 but may be in the form of a coiled wire as shown in FIG. 3. The sensor of FIG. 3 includes no base plate. The electrode may be made of some other noble metal such as palladium or base metal such as nickel, instead of Pt.

Figure 4:
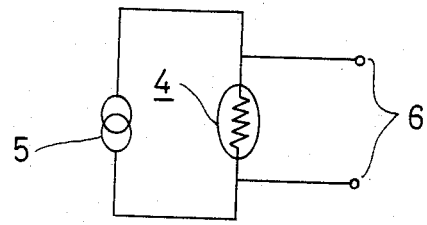
FIG. 4 shows an example of a measuring circuit for driving the gas sensor.

When the gas sensor shown in FIGS. 1 to 3 are to be used, the sensor 4 is connected to a constant-current power supply 5, with voltage detecting terminals 6 provided at opposite ends of the sensor 4 as shown in FIG. 4.

Figure 5:
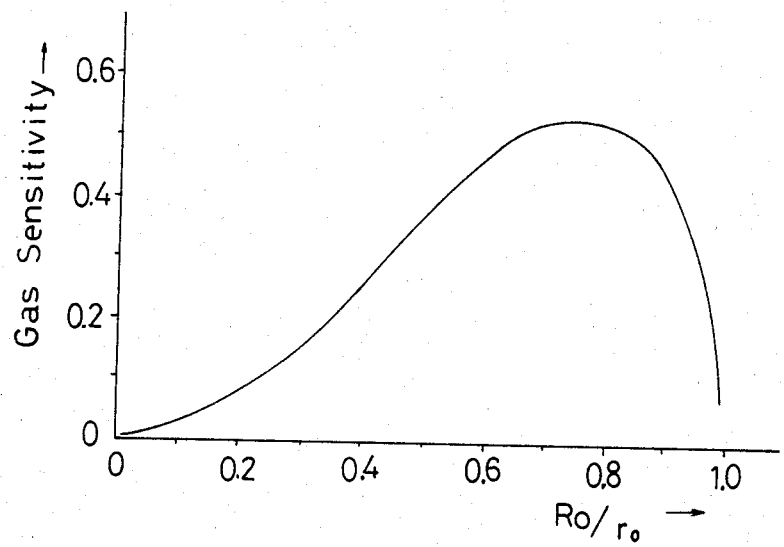
FIG. 5 is a graph showing the relationship between the gas sensitivity and the ratio of combined resistance to the resistance of a platinum resistor.

FIG. 5 shows the relationship between the gas sensitivity and the ratio Ro/ro. The gas sensitivity herein is represented by the apparent variation in the resistance of the gas sensor 4 when the resistance of the sintered $SnO_2$ piece 3 decreases by one figure in response to gas. The gas sensitivity is a value obtained by dividing the $\Delta R$ value below by ro.

$$\Delta R = Ro - Rg$$

wherein Ro and Rg are the resistance values of the gas sensor 4 in the air and in the gas, respectively.

The graph reveals that a desired gas sensitivity of 0.15 is obtained in the range of $0.3 < Ro/ro < 0.98$ and that a still higher sensitivity of 0.30 is achieved in the range of $0.45 < Ro/ro < 0.95$. In other words, the gas sensitivity should be at least 0.15, preferably at least 0.30.

The sintered piece 3 is not limited to $SnO_2$ but may be prepared from ZnO, $Fe_2O_3$, $In_2O_3$ or like oxide semiconductor by sintering.

Second Embodiment

This embodiment makes use of the nature of superfine particles of tin oxide that they are highly amenable to sintering at low temperatures. More specifically, a sintered piece having useful mechanical strength is obtained by sintering a mixture of tin oxide having usual particle sizes of at least 200Å and superfine tin oxide particles (50Å in mean size).

The present embodiment provides a gas sensor wherein such a sintered piece is formed over an electrode and a base plate. The sensor is prepared, for example, by the following process.

First, a hydrate is prepared by precipitation from an aqueous solution of stannic chloride ($SnCl_4$). These primary particles, which are up to 20Å in size, are dehydrated and oxidized in air at 200° to 300° C. and then pulverized into a superfine powder having a mean particle size of 50Å. $SnO_2$ powder of usual particle sizes is mixed with about 30%, based on the combined weight of powders, of the superfine powder, and the mixture is kneaded with water to obtain a paste, Next, a base plate provided with a platinum heater, i.e., an electrode is coated with the paste, which is then dried and sintered at 800° C. for 5 hours, whereby a gas sensor is prepared.

Figure 7:
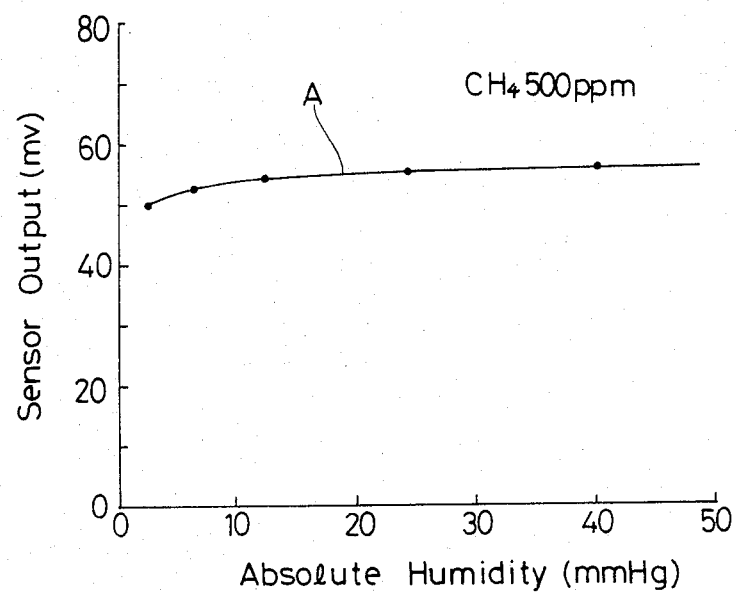
FIG. 7 is a graph similarly showing the humidity dependence of the sensitivity of another gas sensor according to the second embodiment.
Figure 6:
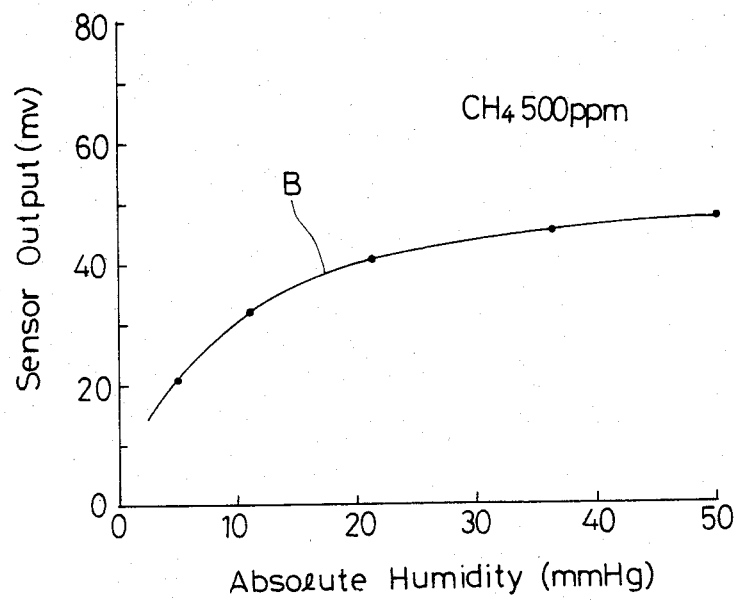
FIG. 6 is a graph showing the humidity dependence of the sensitivity of a known sensor.

When the sensor thus obtained is energized in a gas containing 500 ppm of methane at varying absolute humidities, the sensor gives the voltage output (mV) shown in FIG. 7. FIG. 6 shows the result obtained by checking a known sensor under the same conditions. When compared with FIG. 6, FIG. 7 shows that the sensor of the second embodiment, which has improved strength, is less susceptible to the adverse effect of the absolute humidity of the gas.

It was also proved that another sintering condition under which the two kinds of tin oxide powders were sintered at about 600° C. for 7 hours imparted likewise to the sintered piece an excellent property.

What is claimed is:

1. A gas sensor comprising an electric resistor of noble metal and a sintered piece of a metal oxide covering the electric resistor, the sintered piece being a semiconductor, wherein the ratio of the combined resistance Ro of the resistor and the semiconductor to the resistance ro of the resistor, Ro/ro, is within the range defined by the inequality $0.45 < Ro/ro < 0.95$, wherein the electric resistor is adapted to serve as a heater and also as an electrode for detecting a decrease in the electric resistance of the semiconductor in response to gas adsorption by said semiconductor.

2. A gas sensor as defined in claim 1, wherein the powder forming the sintered piece is an oxide selected from the group consisting of $SnO_2$, ZnO, $Fe_2O_3$ and $In_2O_3$.

3. A gas sensor as defined in claim 2 further comprising a heat-resistant and electrically insulating base plate, the electric resistor being a thin film formed on the base plate.

4. A gas sensor as defined in claim 2 wherein the electric resistor is a coiled wire extending through the sintered piece.

5. A gas sensor as defined in claim 1 wherein the powder forming the sintered piece comprises $SnO_2$ powder of usual particle sizes and a superfine powder of $SnO_2$ and contains about 10 to about 50% by weight of the superfine powder.

6. A gas sensor as defined in claim 5 wherein the sintered piece contains about 30% by weight of the superfine powder.

7. A gas sensor as defined in claim 6 wherein the usual particle sizes are at least about 200Å, and the superfine powder is about 50Å in mean particle size, the component powders being mixed together and sintered at about 600° C. to about 800° C. to form the sintered piece.

* * * * *